United States Patent [19]

Cardinaux et al.

[11] Patent Number: 5,578,567
[45] Date of Patent: Nov. 26, 1996

[54] NASAL PHARMACEUTICAL COMPOSITION

[75] Inventors: François Cardinaux, Seewen; Christine Oechslein, Kaiseraugst; Andreas Rummelt, Oberwil, all of Switzerland

[73] Assignee: Sandoz Ltd., Basle, Switzerland

[21] Appl. No.: 112,024

[22] Filed: Aug. 25, 1993

Related U.S. Application Data

[63] Continuation of Ser. No. 28,852, Mar. 10, 1993, abandoned, which is a continuation of Ser. No. 948,366, Sep. 21, 1992, abandoned, which is a continuation of Ser. No. 762,825, Sep. 19, 1991, abandoned.

[30] Foreign Application Priority Data

Sep. 20, 1990 [GB] United Kingdom ............... 9020544

[51] Int. Cl.⁶ .................. A61K 38/29; C07K 14/635
[52] U.S. Cl. ........................................ 514/012; 530/324
[58] Field of Search ............................... 514/12; 530/324

[56] References Cited

U.S. PATENT DOCUMENTS 5,122,376  6/1992  Aliverh et al. .
5,124,360  6/1992  Larner et al. .................... 514/738
5,190,748  3/1993  Bachynsky et al. ............. 424/78.08

FOREIGN PATENT DOCUMENTS

| 0302772 | 2/1989 | European Pat. Off. . |
| 0312052 | 4/1989 | European Pat. Off. . |
| 0364235 | 4/1990 | European Pat. Off. . |
| 4039656 | 6/1992 | Germany . |
| 63-060940 | 3/1988 | Japan . |
| 63-243033 | 7/1988 | Japan . |
| 2176105 | 12/1986 | United Kingdom . |
| 2193891 | 2/1988 | United Kingdom . |
| 9009167 | 8/1990 | WIPO . |
| 9306845 | 4/1993 | WIPO . |

*Primary Examiner*—Elizabeth Weimar
*Assistant Examiner*—Anish Gupta
*Attorney, Agent, or Firm*—Robert S. Honor; Carl W. Battle

[57] ABSTRACT

A pharmaceutical composition adapted for nasal administration and comprising hPTH or a N-terminal fragment thereof. Preferred carriers are optionally coated celluloses.

8 Claims, No Drawings

NASAL PHARMACEUTICAL COMPOSITION

This is a continuation of application Ser. No. 08/028,852 filed Mar. 10, 1993, which in turn is a continuation of application Ser. No. 07/948,366, filed Sep. 21, 1992, which in turn is a continuation of application Ser. No. 07/762,825, filed Sep. 19, 1991, all of which are now abandoned.

The present invention relates to a novel means for the administration of human parathyroid hormone (hPTH) or a hPTH fragment having a PTH-like activity as well as to novel galenic compositions comprising these compounds.

It is known that hPTH has an anabolic effect on bones and therefore has been stated to be useful for treating e.g. osteoporosis. Anabolic effects on bones have also been shown for N-terminal fragments thereof, e.g. hPTH[1–34] or hPTH[1–38]. However many details of PTH's mechanism of action and properties remain unpublished.

hPTH or a fragment thereof is a peptide susceptible to proteolytic degradation in the gastrointestinal tracts and only passes with difficulty into the body fluids. For this reason parenteral administration has hitherto been used but no form is yet commercially available.

However, injections are always inconvenient and when administration is to be effected at regular intervals and for long term therapy as e.g. in the treatment of post-menopausal osteoporosis, it can cause considerable pain and discomfort to the patient. The finding of viable alternative means of administration of any hPTH fragment causing less inconveniences to the patient and preferably allowing ready self-application while at the same time achieving sufficient efficacy for effective treatment is accordingly a major goal.

The nasal route provides a simple and painless mode of administration which may be easily carried out by the patient himself, for example administering a nasal spray or powder from a nasal applicator. This route is clearly of great advantage over parenteral administration which has generally to be given under medical supervision. However, the absorption of larger peptides across the nasal mucosa is insufficient to achieve effective therapy. Indeed absorption promoters have been proposed for co-administration with such larger peptides in order to enhance absorption.

We have surprisingly found that certain N-terminal hPTH fragments, especially hPTH[1–38] have interesting properties which make them especially useful for nasal administration.

The N-terminal fragment of hPTH as indicated above may comprise at its carboxy end any appropriate group, especially a COOH or CONH$_2$ group.

hPTH fragments of particular interest are e.g. hPTH [1–34]; hPTH[1–35]; hPTH[1–36]; hPTH[1–37]; and hPTH [1–38]. This way of defining the fragment includes the terminal COOH as well as the terminal CONH$_2$ of said fragment. Particularly preferred is hPTH[1–38] which is of formula (Seq. ID No.1)

H—Ser—Val—Ser—Glu—Ile—Gln—Leu—Met—His—Asn—Leu—Gly—Lys—His—Leu—Asn—Ser—Met—Glu—Arg—Val—Glu—Trp—Leu—Arg—Lys—Lys—Leu—Gln—Asp—Val—His—Asn—Phe—Val—Ala—Leu—Gly—X wherein X is OH or NH$_2$, preferably OH.

According to one aspect the present invention provides a pharmaceutical composition adapted for nasal administration and comprising a N-terminal fragment of hPTH selected from hPTH[1–35], hPTH[1–36] and hPTH[1–38] to hPTH [1–41] or an analogue or derivative thereof, preferably hPTH[1–38].

By "analogue or derivative" as used herein is meant any peptide analogous to that of the natural hPTH fragment wherein in the chemical formula one or more amino acid units have been replaced by one or more other amino radical(s) and/or wherein one or more functional groups have been replaced by one or more other functional groups and/or one or more groups have been replaced by one or several other isosteric groups. In general, the term covers all such compounds which exhibit a PTH-like activity but which may, if desired, have a different potency or pharmacological profile.

The pharmaceutical composition may be formulated in conventional manner using excipients compatible with the nasal mucosa, e.g. as described hereinafter.

According to a further embodiment of the invention, there is provided a pharmaceutical composition adapted for nasal administration comprising a hPTH fragment selected from hPTH[1–35] to hPTH[1–41] or an analogue or derivative thereof and a liquid or solid carrier suitable for application to the nasal mucosa.

In a further embodiment, the present invention provides a nasal composition comprising a hPTH fragment selected from hPTH[1–34] to hPTH[1–41] or an analogue or derivative thereof and a liquid or solid carrier suitable for application to the nasal mucosa in the absence of an absorption enhancer or surfactant.

The pharmaceutical composition may be formulated for local administration to the nasal mucosa membrane and is capable of providing a systemic action of said fragments, e.g. in the prevention or treatment of bone conditions which are associated with calcium depletion from bones or increased bone resorption or in which increased calcium fixation to bones is desirable, e.g. osteoporosis.

In a series of specific or alternative embodiments, the present invention further provides:

1. A method of administering a hPTH fragment having PTH-like activity to a subject requiring treatment therewith, e.g. for the purposes of preventive or curative treatment of all bone conditions which are associated with calcium depletion from bones or increased bone resorption or in which increased calcium fixation to bones is desirable, e.g. osteoporosis of various genesis (e.g. juvenile, climacteric, post-climacteric, post-traumatic, caused by old age or by cortico-steroid therapy or immobilsation), fractures, osteopathy, including acute and chronic states associated with skeletal demineralisation, osteo-malacia, periodontal bone loss and skin diseases, which comprises administering hPTH or said hPTH fragment via the nasal route, e.g. in the form of a composition as defined herein;

2. A process for the preparation of a nasal pharmaceutical composition as defined and described herein, comprising bringing the hPTH fragment and the desired components into intimate admixture and working up the composition into a unit dosage form, e.g. as described below.

According to the invention, the pharmaceutical composition intended for delivery to the nasal mucosa, may be liquid or solid, e.g. in nasal spray, drop, gel or powder form, or nasal inserts.

hPTH fragments as defined above for use in the invention may be in free form or in pharmaceutically acceptable salt form or complex or solvate form, e.g. in pharmaceutically acceptable acid addition salt form. Such salts and complexes are known and possess an equivalent degree of activity and tolerability to the free form. Suitable acid addition salt forms for use in accordance with the invention include e.g. the hydrochlorides and acetates.

Where a liquid carrier is present in the composition of the invention, i.e. in the liquid composition of the invention, it is preferably aqueous but can also be chosen from the physiologically acceptable non-aqueous solvents suitable for application to the nasal mucosa. Preferably the liquid carrier is water, aqueous saline, e.g. physiological saline, or an aqueous buffer, e.g. a phosphate/citric acid buffer.

Where a solid carrier is present, i.e. in the solid nasal compositions of the invention, it may be e.g. water-insoluble, sparingly water soluble, water absorbing, water swellable, gel forming or water soluble. Examples of such carriers include e.g. synthetic or semi synthetic polymers optionally crosslinked, such as polyacrylates, e.g. sodium, potassium or ammonium polyacrylate, polylactic acid, polyglycolic acid, copolymers of lactic and glycolic acids, polyvinyl alcohol, polyvinyl acetate, copolymers of vinyl alcohol and acetate, carboxyvinyl polymer, polyvinylpyrrolidone and polyethylene glycol; celluloses such as cellulose, microcrystalline cellulose and α-cellulose, and cellulose derivatives such as methyl cellulose, ethyl cellulose, hydroxyethyl cellulose, hydroxypropyl cellulose, hydroxypropyl methyl cellulose, sodium carboxymethyl cellulose and ethylhydroxy ethyl cellulose; coated celluloses such as coated cellulose, microcrystalline cellulose or α-cellulose; dextrins such as α-, β- or γ-cyclodextrin, dimethyl-β-cyclodextrin, dextrin; starches such as native starches and their derivatives, e.g. hydroxyethyl or hydroxypropyl starch and carboxymethyl starch; polysaccharides such as dextran, crosslinked dextrans, pullulan, alginic acid and salts, hyaluronic acid and salts, pectic acid and salts, phytic acid and phytin; saccharoses such as D-mannitol, glucose, lactose, fructose, inositol, sucrose and amylose; amino acids such as glycine and taurine; polyamino acids such as polyglutamic acid, polyaspartic acid, polyglycine and polyleucine; proteins such as casein, gelatin, gelatin derivatives such as succinyl gelatin, chitin and chitosan; gums such as gum arabic, tragacanth gum and glucomannan and phospholipids; and mixtures thereof.

Preferred carriers are those which improve the contact of the nasal composition with the nasal mucosa or facilitate the diffusion of the drug from the nasal composition to the nasal mucosa, e.g. which prolong the nasal residence time of the nasal composition and/or reduce the distance between the drug or composition and the mucosa.

Preferred solid carriers are polyacrylates, sodium carboxy methyl cellulose, starches and their derivatives, alginic acid and salts, hyaluronic acid and salts, pectic acid and salts, gelatin and its derivatives, gums, polylactic acid and its copolymers, polyvinyl acetate, the celluloses and their derivatives, coated celluloses, crosslinked dextrans, more preferably polylactic acid and its copolymers, polyvinyl acetate, celluloses and their derivatives, coated celluloses and crosslinked dextrans. Particularly preferred is cellulose, α-cellulose, microcrystalline cellulose, coated celluloses, crosslinked dextrans and starches.

By coated celluloses are meant such celluloses which are additionally coated with an agent having bioadhesive properties in order to improve to some extent the bioadhesivity of the cellulose particles to the nasal mucosa.

Preferably the celluloses are coated with a fatty acid ester, more preferably with a glycol or glycerol fatty acid ester, most preferably a glyceride of a saturated or unsaturated $C_{15}-C_{22}$ fatty acid. Particularly preferred coating agents are glycerides of unsaturated $C_{15-22}$ fatty acids, especially monoglycerides. A suitable example of coating agent includes e.g. glycerol monooleate.

The coated celluloses may be prepared according to conventional techniques, e.g. by dissolving the coating agent in an inert solvent, e.g. an alcohol such as ethanol, dispersing the cellulose in the resulting solution, and evaporating the solvent or spray-drying the composition. Preferably the coated cellulose is prepared as a free flowing powder.

Preferably the celluloses are coated with the coating agent in amount of from 1 to 15% by weight of the cellulose, more preferably 1 to 10% by weight.

A particularly preferred coated cellulose is microcrystalline cellulose coated with glycerol monooleate.

For e.g. stability reasons, liquid compositions of the invention preferably have a mildly acid pH, e.g. of from 3.5 to 6.5, preferably 4.5 to 6.5. The required degree of acidity may conveniently be achieved, e.g. by the addition of a buffering agent, e.g. a mixture of citric acid and disodium hydrogen phosphate, or an acid such as HCl or another appropriate mineral or an organic acid, e.g. phosphoric acid.

Solid compositions may also comprise a buffering agent when they are prepared by lyophilization of a liquid composition buffered to a pH value as indicated above.

Liquid and solid compositions of the invention may also contain further additives, e.g. antioxidants such as alkali metal sulfites, alkali metal bisulfites, alkali metal pyrosulfites, sodium thiosulfate, thiodipropionic acid, cysteine in free or salt form, such as cysteine hydrochloride, ascorbic acid, citraconic acid, propyl or ethyl gallate, nordihydroguaiaretic acid, butylated hydroxyanisole or -toluene, tocol, stabilizers such as albumin, e.g. human serum albumin, aprotinin or ε-aminocaproic acid, tonicity adjustors such as nasally acceptable sugars, e.g. glucose, mannitol, sorbitol, ribose, mannose, arabinose, xylose or another aldose or glucosamine, viscosity builders such as methylcellulose, hydroxymethylcellulose, PVA, PVP, polyacrylic acid or natural polymers, preserving agents such as benzalkonium chloride, an alkyl p-hydroxybenzoate (paraben) such as methyl p-hydroxybenzoate and propyl p-hydroxybenzoate, or sodium methylmercurithiosalicylate (Thiomersal).

According to another embodiment, the invention provides a pharmaceutical composition adapted for nasal administration and comprising a fragment of hPTH selected from hPTH[1–35] to hPTH[1–41], an absorption enhancer or surfactant and optionally a liquid or solid carrier, e.g. a cellulose or coated cellulose as disclosed hereinbefore. More particularly there is provided a nasal composition comprising hPTH[1–34] and an absorption enhancer or surfactant which is a glycyrrhizinate, and optionally a solid or liquid carrier, e.g. an optionally coated cellulose.

By absorption enhancer is meant a compound which acts to increase absorption across the nasal mucosa, e.g. by interacting with the mucosal membrane components and/or by increasing permeability of the mucosal membrane.

Suitable absorption enhancers include e.g. choline esters, e.g. as disclosed in EP-A-214898, acyl carnitines, e.g. as disclosed in EP-A-215697, aldoses and glucosamines, ascorbates and salicylates, e.g. as disclosed in EP-A-37943, α-cyclodextrin, e.g. as disclosed in EP-A-94157, pyroglutamate esters, e.g. as disclosed in EP-A-173990, chelating agents, e.g. as disclosed in U.S. Pat. No. 4,476,116, polyacrylic acid gel base, sodium glycyrrhetinate, sodium caprate, ammonium tartrate, a glycyrrhizinate, e.g. sodium or ammonium glycyrrhizinate, e.g. as disclosed in EP-A-327756, glycine or γ-aminolevulinic acid.

The contents of all the above publications including the specific examples of absorption enhancers are specifically incorporated herein by reference.

If desired, the liquid and solid compositions of the invention may also comprise a surfactant, for example:

Bile salts such as sodium taurocholate, sodium cholate, sodium deoxycholate, sodium chenodeoxycholate, lysine chenodeoxycholate, sodium glycocholate, sodium glycodeoxycholate, lysine taurocholate, and sodium taurodeoxycholate;

Cationic surfactants such as the long chain amine condensation products with ethylene oxide and quaternary ammonium compounds, for example cetyl trimethyl ammonium bromide and dodecyl dimethyl ammonium bromide;

Anionic surfactants such as alkylbenzenesulfonates, N-acyl-n-alkyltaurates, α-olefin sulfonates, sulfated linear primary alcohols and sulfated polyoxyethylene alcohols (straight chain alcohols);

Non ionic surfactants such as polyoxyalkylene higher alcohol ethers, polyoxyalkylene alkylphenols, long chain carboxylic acid esters including glycerol esters of natural fatty acids, propylene glycol, sorbitol, and polyoxyethylene sorbitol esters e.g. Polysorbate$^R$ 80;

Amphoteric surfactants such as imidazoline carboxylates, sulfonates and the like; and Natural or synthetic phospholipids, such as phosphatidyl choline, egg or soja lecithine, lysophosphatidyl choline, lysophosphatidyl glycerol and the like.

Most of these surfactants have also absorption enhancing properties and may also be used as absorption enhancers.

Desired viscosity for the liquid compositions of the invention will depend on the particular form for administration, e.g. whether administration is to be by nasal drops or nasal spray.

For nasal drops an appropriate viscosity is from about 2 to $400 \times 10^{-3}$ Pa.s. For nasal sprays the viscosity may preferably be less than $2 \times 10^{-3}$ Pa.s.

The particle size of the components including the carriers, e.g. the cellulose carrier, in the solid nasal composition of the invention may be from 5 to 500μ, preferably from 10 to 250μ, more preferably from 20 to 200μ.

The liquid compositions of the invention may be prepared by bringing into intimate admixture said PTH fragment in the liquid carrier optionally together with the further ingredients. Preferably the resulting mixture is then lyophilized and dissolved in water or aqueous saline for use in a liquid form according to the invention.

The solid nasal composition of the invention may be prepared in conventional manner. The hPTH fragment may be admixed with the carrier particles, e.g. a polymer base or cellulose product in conventional manner, optionally with further ingredients as indicated above e.g. an absorption enhancer or surfactant such as disclosed. The PTH fragment may be in solution e.g. an aqueous or alcoholic solution when being mixed with the carrier particles and the solvent evaporated, e.g. under freeze-drying or spray drying. Such drying may be effected under the conventional conditions. Alternatively the mixture may be compacted or granulated and then be pulverized and/or sieved. If desired the particles may be coated.

According to a preferred embodiment of the invention, the nasal composition is prepared by lyophilisation. A homogeneous solution, preferably aqueous, containing the hPTH fragment and optionally further ingredients, e.g. as indicated above, is prepared and then submitted to lyophilisation, e.g. in analogy with known lyophilisation procedures, and to subsequent drying. The resulting powder may then be dissolved in a liquid excipient or carrier before administration, e.g. to reconstitute nasal drops, gel or spray. Alternatively it may be administered as such in the form of lyophilized powder or it may be mixed with further ingredients, e.g. as indicated above. For example, a lyophilized powder comprising the active ingredient but free of any carrier may be prepared and then admixed with the desired carrier or mixture of carriers.

In another aspect the present invention provides a porous solid nasal insert having a hPTH fragment as disclosed above dispersed therein. In yet another aspect the present invention provides a solid nasal insert comprising a porous matrix comprising gelatine and/or hydroxypropylmethylcellulose and a hPTH fragment.

The nasal insert may be produced by any conventional method, e.g. by a) producing a distribution of a hPTH fragment throughout a porous matrix comprising gelatine and/or hydroxypropylmethylcellulose, e.g. by lyophilising a liquid containing a polymer capable of forming a matrix, and a hPTH fragment; or b) distributing a hPTH fragment throughout a nasal insert, for example by soaking a sponge in an aqueous solution at e.g. room temperature and evaporating off the solvent, e.g. by freeze-drying.

By the term "nasal insert" is to be understood, e.g. a device which is sized, shaped and adapted for placement and retention into the naris: intended for insertion into the naris; or which is formed, shaped or otherwise adapted for insertion into and/or retention in the naris; or which is shaped to substantially conform to the internal surface of the naris; or which is provided together with instructions to effect insertion into the naris. The insert may be retained in the naris, but flushed by the nasal mucus, and may be designed to release the active agent at the same place in the naris. Suitable nasal insert types include nasal plugs, tampons and the like. Conveniently the volume and porosity of the insert are chosen such that it is retained in the naris, but breathing is not significantly inhibited. Suitable dimensions are e.g. from about 0.05 to about 1 cm$^3$, e.g. about 0.5 to about 0.8 cm$^3$. The shape may be approximately e.g. a cylinder, a cone, a cube or sphere.

The hPTH fragment may be carried on the insert, e.g. by adsorption onto the surface thereof, or in the insert, e.g. by adsorption, or by any other convenient means, e.g. carried in combination with one or more nasally acceptable diluents or vehicles in the form of a coating, e.g. solid or semi-solid coating, upon the surface on the insert.

Alternatively, where the insert itself comprises a soluble or semi-soluble material, e.g. water-soluble polymers, or material otherwise degradable within the naris, for example a nasally acceptable proteinaceous material such as gelatin, the hPTH fragment may be present in solid form, e.g. in the form of lyophilisate dispersed within the insert, e.g. distributed throughout the matrix.

Preferably the hPTH fragment is carried, e.g. by adsorption, in the insert and is suitably distributed throughout the insert.

Inserts in accordance with the invention are capable of releasing the peptide carried to the surface of the nasal mucosa. For this purpose they will preferably be so shaped or formed as to conform to the internal surface of the naris, e.g. so as to enable maximum contact between the surface of the insert and the nasal mucosa. Moreover, where the hPTH fragment is retained in the insert, e.g. by absorption, its characteristics e.g. the absorption characteristics of the material of which it is comprised, will suitably be such as to allow ready passage of the peptide to the surface of the insert following progressive uptake by the nasal mucosa from the insert surfaces.

Where the fragment is retained, e.g. by adsorption, in the insert, the insert may comprise any appropriate, e.g. nasally acceptable material, providing a porous matrix or reticulum in the interstices of which the peptide may be retained, e.g. absorbed. The material is conveniently elastic so it can be retained in the naris without discomfort. It may be for example, fibrous material, such as cotton wool or sponge material, such as natural or synthetic sponge.

If desired, the material may swell a little, e.g. increase in volume by about 50%, on administration.

The material from which the insert is made may be for example a water soluble polymer. Preferably the polymer is easily wettable by the nasal mucous. In the naris it may be biodegradable and, it may even dissolve slowly, e.g. over up to one or more days. It may have to be removed after the dose of active agent has been administered. An example is lyophilised absorbable gelatine sponge. If desired the matrix may dissolve by the time or shortly after the dose of active agent has been administered. Examples include water-soluble acrylate polymers and cellulose derivatives such as cellulose, e.g. hydroxypropylcellulose and especially hydroxypropylmethyl cellulose. Alternatively water-insoluble crystalline cellulose may be used.

The characteristics of the matrix material used, e.g. viscosity or molecular weight should be chosen such that these resultant insert is easy to handle and store. Typical molecular weights for hydroxypropyl methylcellulose are from about 9,000 to 15,000 and a viscosity e.g. 4 to around 15 cp, for a 2% solution.

Another suitable material is a gelatin sponge material. Specifications have been laid down in the US Pharmacopoeia for absorbable gelatine sponges e.g. for hemostatis in surgical procedures and such sponges are preferred. Such sponges may be produced, e.g. by vigorously whipping and aqueous solution of pure gelatine to produce a foam, drying the foam under controlled conditions to give a sponge, cutting up the sponge and sterilizing the cut-up pieces. Suitable sizes are from about 5×5×5 to about 10×10×10 mm. The sponge is compressed by hand before use and is resorbed over a few hours. An especially suitable sponge material for use in the preparation of nasal inserts in accordance with the invention is the product SPONGOSTAN$^R$ available from A/S Ferrosan, 5 Sydmarken, DK-2860 Soeborg, Denmark.

Alternative polymers are e.g. hydroxypropylcellulose or polyvinylpyrrolidone.

As indicated above the insert preferably has a porous structure. Conveniently the nasal mucous can wet the insert and the active agent may diffuse through the pores in the insert to the surface of the naris.

The pores of the insert may have a diameter of for example a few microns to about 100μ. The pores of a lyophilized absorbable gelatin sponge may be for example from about 5 to 100μ. The pore size may for example be from about 5 to about 10μ.

In sponge material the pores may be tortious. When the insert is produced under lyophilisation the pores may be approximately linear.

Preferably the insert contains a water-soluble sugar or like excipient to provide a stable structure to the insert. Examples of suitable sugars include lactose, saccharose, and mannitol. Preferably the weight ratio sugar to other material is from about 0.1 to 1 to about 10 to 1.

A preferred insert comprises a water-soluble polymer such as hydroxypropylmethyl cellulose and lactose. Under electron microscopy a lyophilized sample appears to comprise laminar sheets each having pores therein. The pores extend substantially throughout the sample.

Where a hPTH fragment is retained in the insert, e.g. by absorption, it will conveniently be carried in dilute form, e.g. in the form of a composition comprising the active agent together with a nasally acceptable fluid, e.g. liquid, diluent or vehicle therefor. Suitably such compositions will comprise the agent in the form of a solution, suspension, dispersion or the like. Preferably such compositions will comprise the agent in aqueous solution.

The insert is preferably formed under substantially microorganism free or sterile conditions. In one preferred variante a solution of the active agent is lyophilized. The insert may be preformed or formed during the lyophilization process, e.g. from a solution of the insert material.

The lyophilization may be effected under conventional conditions, preferably at low temperatures, e.g. ca. about $-100°$ C. to about $-10°$ C. Conventional pressures, e.g. ca. about 0.01 mm to about 0.2 mm Hg may be used.

Lyophilization may produce an outer layer of very fine pores which may be spongy. This outer layer may be about 10 to 100μ thick. If desired its formation may be avoided by effecting the lyophilization at very low temperature. Alternatively it may be removed by rubbing.

The amount of hPTH fragment to be administered in accordance with the method of the invention will, of course, depend on the particular compound chosen (i.e. terminal COOH or $CONH_2$, in free, salt, solvate or complex form), the conditions to be treated, the desired frequency of administration and the effect desired. The bioavailability of the compositions of the invention may be determined in conventional manner, e.g. radioimmunoassay. Doses may be chosen to be equipotent to the injection route. The amount of active compound will generally be chosen to provide effective treatment on administration once or 2 to 4×/day. For this purpose the active compound is suitably present in an amount such as to provide a free hPTH fragment (with terminal COOH or $CONH_2$) concentration of from about 0.01–100 mg per administration, preferably from about 0.1–10 mg.

The proportion of each further component in the nasal composition of the invention may vary depending on the components used. For example the amount of carrier may be in the range of from 0.1 to 99.9% by weight of the total weight or volume of the composition. A preferred solid composition comprises from 1 to 30 mg carrier per dosage, particularly 4 to 20 mg.

When present, the amount surfactant may be in the range from about 0.01 to about 10% or higher and preferably about 0.05 to about 1.0% by weight of the total volume or weight of the composition, the amount depending on the surfactant used. The amount is generally kept as low as possible since above a certain level no further enhancement of absorption can be achieved and also too high of a surfactant level may cause irritation of the nasal mucosa.

The amount of absorption enhancer may be at least 0.1%, suitably in the range from about 0.5 to 10% of the total weight of the composition. Where the composition is liquid, the absorption enhancer may suitably be present in an amount of from 0.1 to 5% w/v of the total composition.

Preserving agents may be present in an amount of from about 0.002 to 0.02% by weight of the total weight or volume of the composition.

Compositions in accordance with the present invention may be administered in any appropriate form. They may be packaged for administration in conventional manner, preferably in a nasal applicator, conveniently in such a way as to deliver a fixed dose of active ingredient. For administration in drop form such compositions will suitably be put up in a container provided e.g. with a conventional dropper/closure device, e.g. comprising a pipette or the like, preferably delivering a substantially fixed volume of composition/drop. For administration as a spray, such compositions will be put up in an appropriate atomising device, e.g. in a pump-atomiser or the like. The atomising device will be provided with appropriate means for delivery of the aqueous spray to the naris. Preferably it will be provided with means ensuring delivery of a substantially fixed volume of composition/actuation (i.e. per spray-unit).

Alternatively the spray may be bottled under pressure in a novel aerosol device.

Conveniently the device administers a metered dosage. The propellant may be a gas or a liquid, e.g. a fluorinated and/or chlorinated hydrocarbon. The spray composition may be suspended or dissolved in a liquid propellant. Stabilizing and/or suspending agents and/or co-solvents may be present. If desired a powder or liquid may be filled into a soft or hard gelatine capsule or in a single dose device adapted for nasal administration. The powder may be sieved before filled into the capsules. The applicator may have means to break open the capsule.

The powdery nasal composition can be directly used as a powder for a unit dosage form. If desired the powder can be filled in capsules such as hard gelatine capsules. The contents of the capsule or single dose device may be administered using e.g. an insufflator. Preferably it will be provided with means ensuring dosing of a substantially fixed amount of composition/actuation.

The pharmaceutical compositions of the invention adapted for nasal administration are locally tolerated: no adverse effects on nasal septal cartilage are observed when e.g. [1–38]hPTH is nasally administered to rats for three weeks at a daily dose of 100 μg/kg dissolved in a total volume of 40 μl (buffered with citric acid/phosphate).

The nasal compositions of the invention are surprisingly stable, e.g. in the light of its structure and chain length, e.g. over one year at a temperature of +5° C.

On administration the nasal compositions of the invention provide a delivery with a rapid onset of hPTH fragment, thus generating on repeated administration a pulsatile plasma profile which is particularly appropriate for the anabolic PTH therapy.

The nasal compositions which are e.g. surprisingly stable and well tolerated have a fast onset of action and/or may only require administration twice a day or even less frequently despite the complex structure and length of the hPTH fragment.

The nasal pharmaceutical compositions of the invention are particularly indicated for long term therapy, e.g. for the treatment of osteoporosis.

In accordance with the foregoing the present invention further provides a container containing a pharmaceutical composition for nasal administration as defined and described above, in liquid or powder form, and an applicator device containing said pharmaceutical composition and provided with means enabling application of the contained composition, in liquid (including the dissolution of the lyophilisate) or powder form, to the nasal mucosa.

Furthermore, it has been found that the coated celluloses which are novel are also useful e.g. as carriers for nasal administration of any active agent, particularly a peptide.

In accordance with the foregoing the present invention further provides a powdered pharmaceutical composition adapted for nasal administration and comprising a physiologically active peptide as an active ingredient and a coated cellulose, e.g. as disclosed hereinbefore.

Preferred coated celluloses and their preparation are as described hereinbefore.

The coated celluloses have particularly interesting properties for the reliable and efficient nasal administration of active agents.

The physiologically active peptides include e.g. peptide hormones, proteins and enzymes which have physiological activity such as hPTH, calcitonins, calcitonin gene related peptides (CGRP), insulin, somatostatin, e.g. octreotide, vapreotide or angiopeptin, growth hormone, secretin, gastrin, vasopressin, oxytocin, glucagon, adrenocorticotropic hormone (ACTH), thyroid-stimulating hormone (TSH), prolactin, luteinizing releasing hormone (LHRH), neurotensin, lymphokin, monokine e.g. interferon or interleukins, superoxidase dismutase, and derivatives or analogues thereof.

Preferred peptides and their analogues or derivatives are those having a molecular weight within the range of 1,000 to 10,000. More preferred are hPTH (as indicated above), calcitonins e.g. salmon calcitonin, eel calcitonin and chicken calcitonin, and somatostatin, and the derivatives or analogues thereof.

The powdered peptide composition may contain further ingredients, e.g. as required for formulation of the powdered preparation, for example as described above for the hPTH nasal composition, e.g. absorption enhancers, buffering agent, preservatives, etc.

The proportion of the components in the powdered peptide composition may vary, e.g. depending on the peptide used. Doses may be chosen to be equipotent to the injection route. The amount of active peptide will generally be chosen to provide effective treatment on administration once or 2 to 4 times/day. The physiologically active peptide may suitably be present in an amount such as to provide a free peptide concentration of from 0.01 to 100 mg per administration, preferably 0.1 to 10 mg. The coated celluloses present in the powdered composition may be of from about 0.05–99.995% by weight, preferably about 0.5–99.99% by weight of the composition.

Preferably the powdered peptide compositions have a particle size as disclosed above.

The powdered peptide compositions may be prepared as disclosed herein before.

The [1–36] fragment of hPTH is a novel compound and also forms part of the invention. Accordingly the invention also provides in another aspect a peptide of formula I (Seq. ID No.2)

H—X$_1$—Val—Ser—Glu—Ile—Gln—Leu—Met—His—Asn—
Leu—Gly—Lys—His—Leu—Asn—Ser—Met—Glu—Arg—Val—
Glu—Trp—Leu—Arg—Lys—Lys—Leu—Gln—Asp—Val—His—
Asn—Phe—Val—X$_2$—X$_3$ wherein X$_1$ is Ser or Ala, X$_2$ is Leu or Ala, and X$_3$ is OH or NH$_2$.

Compounds of formula I may exist e.g. in free form, salt form or in the form of complexes thereof. Acid addition salts may be formed with e.g. organic acids, polymeric acids and inorganic acids. Such acid addition salt forms include e.g. the hydrochlorides and the acetates. Complexes are e.g. formed from the compound of the invention on addition of inorganic substances, e.g. inorganic salts or hydroxides such as Ca- and Zn-salts, and/or an addition of polymeric organic substances.

The present invention also provides a process for the production of the compounds of formula I. They may be produced e.g. by methods known in the art of peptide chemistry. They may be prepared in a stepwise manner either in solution or using the solid phase synthesis process. They may also be prepared by genetic engineering.

The compounds of formula I may be produced for example as follows:

a) removing at least one protecting group which is present in a compound of formula I in protected form; or b) linking together by an amide bond two peptide fragments each of them containing at least one amino acid in protected or unprotected form, wherein the amide bond is in such a way that the desired amino acid sequence of formula I is obtained, and then effecting optionally stage a) of the process, and recovering the compounds thus obtained in free form or in salt form.

The above reactions may be effected in analogy with known methods, e.g. as described in the following example. Where desired, in these reactions, protecting groups which are suitable for use in peptides may be used for functional groups which do not participate in the reaction. The term protecting group may also include a polymer resin having functional groups.

Compounds of formula I in free form or in the form of pharmaceutically acceptable salts and complexes exhibit valuable pharmacological properties as indicated in animal test and are therefore indicated for therapy.

The biological activity of the compounds of formula I is assessed in vitro by measuring their ability of stimulating the synthesis of cyclic AMP according to the method of Aurbach and Marcus in Endocrinology, 85, 801–810 (1969) or by determining their effect on the serum calcium in chicken after intravenous administration in accordance with the in vivo bioassay method described by Parsons et al. in Endocrinology, (1973), 92, 454–462. Compounds of formula I are active in these tests.

More particularly, the compounds of formula I show PTH agonist activity as indicated e.g. by stimulating bone resorption in fetal rat long bones as follows:

Cultures of fetal rat long bones are performed as described by Raisz in J. Clin. Invest 44:103. Nineteen-day-old fetal rat fore-limb bones, previously labeled in utero with $^{45}$Ca, are dissected free of surrounding cartilage, muscle and connective tissue. The bones are precultured in BGJ medium for 24 hours and then transferred to 0.5 ml BGJ supplemented with BSA (1 mg/ml) and cultured in the presence of a compound of formula I for a period of 5 days, with a change of medium at 2 days. The $^{45}$Ca content of the 2 and 5-day media and of 5% trichloroacetic acid extracts of the bone is measured by liquid scintillation counting. The percent of total bone $^{45}$Ca released at 2 and 5 days is indicative of the bone resorption stimulating activity of the compounds to be tested. Compounds of formula I stimulate bone resorption in this test at a concentration of $10^{-10}$ to $10^{-7}$M.

The compounds of formula I also regulate bone modeling as indicated by studies of collagen turnover in bone cultures:

Half calvariae from 21-day-old fetal rats are cultured in the presence of the compound to be tested for 48 hours. During the first 4 hours of the treatment period the calvaria are labelled with 10 µCi/ml [$^3$H]-proline. Culture, hydrolysis and derivatization are performed as disclosed by S. Rydziel and E. Canalis in Calcif. Tissue Int. 44:421–424, 1989. At the end of the derivatization step, samples are analyzed for the presence of [$^3$H]proline/[$^3$H]hydroxyproline by HPLC as described by S. Rydziel et al. At a concentration of $10^{-10}$ to $10^{-7}$M compounds of formula I decrease the levels of [$^3$H]hydroxyproline released to the calvarial culture medium over 48 hours.

Furthermore, the compounds of formula I stimulate bone cell proliferation in cultured rat calvariae, e.g. by stimulating [$^3$H]thymidine incorporation into deoxyribonucleic acid (DNA).

Half calvariae from 21-day-old fetal rats are cultured as described by E. Canalis et al in J. Clin. Invest., 83, 60–65 (1989) for 24–72 hours after a pre-culture of 24 hours. The compound to be tested is added directly to BGJ culture medium. DNA synthesis is assessed by measuring the incorporation of [$^3$H]thymidine into acid-soluble bone fraction. At the end of the culture, bones are pulsed with 5 µCi/ml [methyl-$^3$H]thymidine for 2 hours and washed in PBS. To determine calvarial dry weight, the bones are extracted with 5% (w/v) trichloroacetic acid (TCA), acetone and ether, dried and weighed. After weighing the bones were rehydrated and digested in 0.9 ml NCS tissue solubilizer. The digest is counted e.g. in the presence of 10 ml 4.2% Liquifluor in toluene. Results are expressed as disintegrations per minute per calvarial dry weight. Compounds of formula I are active in this test at a concentration of $10^{-10}$ to $10^{-7}$M.

The compounds of formula I are accordingly indicated for preventing or treating all bone conditions which are associated with calcium depletion or increased calcium resorption or in which increased calcium fixation to bones is desirable, e.g. osteoporosis of various genesis (e.g. juvenile, climacteric, post-climacteric, post-traumatic, caused by old age or by cortico-steroid therapy or immobilisation), fractures, osteopathy, including acute and chronic states associated with skeletal demineralisation, osteo-malacia, periodontal bone loss and skin diseases, and for treating hypoparathyroidism.

The compounds of formula I are particularly indicated for preventing or treating osteoporosis of various genesis.

For these indications, the appropriate dosage will, of course, vary depending upon, for example, the host, the mode of administration and the severity of the conditions being treated. However, in general, satisfactory results in animals are indicated to be obtained at daily dosages from about 0.001 to about 10 mg/kg animal body weight. In larger mammals, for example humans, an indicated daily dosage is in the range from about 0.01 to about 100 mg of the compounds of formula I, conveniently administered in divided doses up to 4 times a day in unit dosage form containing for example from about 2.5 µg to 50 mg of the compound or in sustained release form.

The compounds of formula I may be administered in free form or in pharmaceutically acceptable salt form or complexes. Such salts and complexes may be prepared in conventional manner and exhibit the same order of activity as the free compounds. The present invention also provides a pharmaceutical composition comprising a compound of formula I in free base form or in pharmaceutically acceptable salt form or complex form in association with a pharmaceutically acceptable diluent or carrier. Such compositions may be formulated in conventional manner. The compounds of formula I may be administered by any conventional route, for example parenterally e.g. in form of injectable solutions or suspensions, enterally, e.g. orally, for example in the form of tablets or capsules or a suppository form or in a nasal form, e.g. as disclosed above.

In accordance with the foregoing the present invention further provides:

a) a compound of formula I or a pharmaceutically acceptable salt or complex thereof for use as a pharmaceutical;

b) a method for improving bone formation, e.g. for preventive or curative treatment of all bone conditions which are associated with calcium depletion in bones or increased bone resorption or in which increased calcium fixation to bones is desirable, e.g. osteoporosis e.g. of various genesis (e.g. juvenile, climacteric, post-climacteric, post-traumatic, caused by old age or by cortico-steroid therapy or inactivity), fractures, osteopathy, including acute and chronic states associated with skeletal demineralisation, osteo-malacia, periodontal bone loss and skin diseases, in a subject in need of such treatment, which method comprises administering to said subject an effective amount of a compound of formula I or a pharmaceutically acceptable salt or complex thereof;

c) a compound of formula I or a pharmaceutically acceptable salt or complex thereof for use in the preparation of a pharmaceutical composition for use in the method as in b) above.

The compounds of formula I may also be employed as adjunct or adjuvant to other therapy, e.g. a therapy using a bone resorption inhibitor, for example as in osteoporosis therapy, in particular a therapy employing a calcitonin or an analogue or derivative thereof, e.g. salmon, eel or human calcitonin, asteroid hormone, e.g. an oestrogen, a fluoride, calcium or a phosphate or any combination thereof.

When the compounds of formula I are administered in conjunction with, e.g. as an adjuvant to bone resorption inhibition therapy, dosages for the co-administered inhibitor will of course vary depending on the type of inhibitor drug employed, e.g. whether it is asteroid or a calcitonin, on the condition to be treated, whether it is a curative or preventive therapy, on the regimen and so forth.

In accordance with the foregoing the present invention provides in a yet further aspect:

d) a method for improving bone formation, e.g. for preventive or curative treatment of calcium depletion, for example for preventing or treating any of the specific conditions or diseases hereinbefore set forth, in a subject in need of such a treatment which method comprises administering to said subject an effective amount of a) a compound of formula I and b) a second drug substance, said second drug substance being a bone resorption inhibitor, for example asteroid hormone, a calcitonin or an analogue or derivative thereof, a fluoride or a phosphate.

The following examples illustrate the invention. The following abbreviations are used.

DMF=dimethylformamide
DCM=dichloromethane
Fmoc=9-fluorenylmethoxycarbonyl
HOBt=1-hydroxybenzotriazole
Pmc=2,2,5,7,8-pentamethylchroman-6-sulphonyl
TFA=trifluoroacetic acid
Trt=trityl=triphenylmethyl
HSA=Human Serum Albumin

EXAMPLE 1

| Ingredient | Quantity (per ml) | |
|---|---|---|
| | A | B |
| [1-38]hPTH | 0.8 mg | 0.04 mg |
| Mannitol | 3.6 mg | 40.0 mg |
| HSA | 0.45 mg | 5.0 mg |
| Distilled Water | to end volume of 1 ml | |

[1-38]hPTH and the mannitol are dissolved in water and the pH is adjusted to 5.5 by addition of citric acid/Na$_2$HPO$_4$ buffer. The resulting solution is submitted to rapid freezing at a low temperature, e.g. ca. −40° C. for a period of ca. 12 hours. Lyophilisation is then effected under high vacuum for ca. 24 hours. Thereafter the lyophilisate is dried under vacuum at a temperature not exceeding 15° C.

Composition B exhibits a stability over one year when stored at +5° C.

EXAMPLE 2

| Ingredient | Quantity |
|---|---|
| [1-38]hPTH | 8.0 mg |
| Glycine | 22.0 mg |
| Sucrose | 6.0 mg |
| Distilled Water | to end volume of 0.1 ml |

The resulting solution has a pH of 6.23. This solution is lyophilised and dried as disclosed in Example 1.

EXAMPLE 3

| Ingredient | Quantity |
|---|---|
| [1-38]hPTH | 10.0 or 40.0 mg |
| KH$_2$PO$_4$ | 1.76 mg |
| Na$_2$HPO$_4$ | 0.07 mg |
| Human Serum Albumin | 5.0 mg |
| Distilled Water | to end volume of 0.1 ml |

This solution (pH=5.4) is lyophilised and dried as disclosed in Example 1.

EXAMPLE 4

| Ingredient | Quantity |
|---|---|
| [1-38]hPTH | 0.04 mg |
| Citric acid | 1.92 mg |
| Na$_2$HPO$_4$ | 3.31 mg |
| Human Serum Albumin | 5.0 mg |
| Distilled Water | to end volume of 0.1 ml |

This solution is lyophilised and dried as disclosed in Example 1. Citric acid and Na$_2$HPO$_4$ are used to buffer the solution to pH 5.4.

EXAMPLES 5 TO 8

| Composition (mg/capsule) | Ex. 5 | Ex. 6 | Ex. 7 | Ex. 8 |
|---|---|---|---|---|
| a. [1-38]hPTH | 0.8 | 0.8 | 0.8 | 0.8 |
| b. Citric acid | — | — | 0.19 | 0.19 |
| c. Na$_2$HPO$_4$ | — | — | 0.33 | 0.33 |
| d. HSA | — | — | 0.5 | 0.5 |
| e. Mannitol | 19.2 | — | 4.0 | 4.0 |
| f. Microcrystalline Cellulose | — | 19.2 | 14.27 | — |

The microcrystalline cellulose (Avicel PH 101, Registered Trade Mark) has a particle size distribution of approximately 38–68μ. The compositions of Examples 5 to 7 are obtained in the form of a powder; they are sieved and then filled into capsules.

In Example 7 ingredients a. to e. are dissolved in 1 ml water and the resulting solution is filtrated and then lyophilized. Ingredient f. is admixed with the lyophilized mixture, thus giving a powder ready for nasal administration.

In Example 8 all the ingredients are dissolved in 1 ml water and the resulting solution is filtrated and lyophilized. The powder is then dissolved in an appropriate device in 90 µl water before administration to reconstitute drops or a spray.

The compositions of Examples 5 to 7 can be administered nasally by an insufflator and the composition of Example 8 by a drop device or a pump atomizer device. Each actuation administers 0.8 mg [1–38]hPTH in either 20 mg powder or 0.1 ml water. In Examples 7 and 8 the solution is buffered by addition of the disclosed citric acid/$Na_2HPO_4$ buffer.

EXAMPLE 9

17.4 mg microcrystalline cellulose are coated with 1.8 mg glyceryl monooleate as described below, mixed with 0.8 mg [1–38]hPTH and then sieved.

The coated cellulose is prepared as follows: 18 mg glyceryl monooleate is dissolved in 1 ml ethanol. 174 mg microcrystalline cellulose are then dispersed in it and the ethanol is evaporated. A free flowing coated microcrystalline cellulose powder is obtained.

BIOAVAILABILITY STUDIES FOR EXAMPLES

Compositions of Examples 1A, 6 and 9 are administered nasally to rhesus monkeys (n=5) at a dose of 100 µg/kg [1–38]hPTH. A reference composition comprising 0.04 mg [1–38]hPTH
40.0 mg mannitol
5.0 mg HSA and buffered to pH 5.5 with $Na_2HPO_4$/citric acid is administered i.v. at a dose of 10 µg/kg.

Blood is taken after 10, 20, 30, 45, 60, 90, 240 and 360 min after administration and stored deep frozen at −80° C. until analysed. [1–38]hPTH concentrations in serum are analysed using radioimmunoassay techniques providing a limit of detection of 0.2–0.1 ng/ml. In addition urine is collected and stored deep frozen at −80° C. until analysis of cAMP by RIA techniques.

Following pharmacokinetic parameters are obtained:

| | Cpmax (ng/ml) | t max hr | AUC (0–6 hr) ng ml$^{-1}$ hr | Bioavailability % |
|---|---|---|---|---|
| Ref | 21.24 | 0.17 | 7.43 | 100 |
| Ex. 1A | 2.79 | 0.37 | 1.76 | 2.20 |
| Ex. 6 | 3.36 | 0.63 | 3.76 | 6.17 |
| Ex. 9 | 3.03 | 0.57 | 2.60 | 4.97 |

Bioavailability levels based on serum level concentration and cumulative urinary excretion indicate that therapeutic [1–38]hPTH serum levels are achieved in monkeys.

EXAMPLE 10: Nasal lyophilisate inserts

| [1-38]hPTH | 0.8 mg |
|---|---|
| Lactose | 2.0 mg |
| HMPC | 3.0 mg |

30 g of water are heated to 70° C. 1.5 g of HPMC are added. The suspension is cooled to room temperature and 1 g lactose are added. 15 g pure water are used to dissolve the hPTH fragment. The liquids are mixed and water added to 50 ml. The solution is filtered through 0.2µ mesh and pipetted in 0.1 ml lots into depressions (5 mm) in an aluminium plate.

The plate is cooled to −35° C. for 4 hours, then lyophilisation starts for 40 hours at −10° C. and continues for 24 hours at +15° C. After raising the temperature in the lyophilizer to room temperature, the resultant lyophilized blocks are carefully removed from the plate and inserted into a 1 ml syringe, the needle end of which has been cut off about 3 mm from the end. Each block weights about 5 mg.

The resultant insert is stable and easily disolvable in water. It is a uniform lyophilizate sized about 5 mm in diameter and about 6 to 7 mm in length.

EXAMPLE 11

The procedure of Example 1, 6, 7, 8 or 9 is repeated but using [1–37]hPTH instead of [1–38]hPTH.

EXAMPLE 12

The procedure of Example 6, 7, 8 or 9 is repeated but using [1–34]hPTH instead of [1–38]hPTH.

EXAMPLE 13

By following the procedure of Example 8 a composition comprising

| [1-34]hPTH or [1-37]hPTH or [1-38]hPTH | 0.8 mg |
|---|---|
| Ammonium glycyrrhizinate | 0.2 mg |
| Citric acid | 0.19 mg |
| $Na_2HPO_4$ | 0.33 mg |
| Distilled water | to 0.1 ml | is prepared. As disclosed in Example 8, the mixture is lyophilized and dissolved in water Just before administration.

EXAMPLE 14: hPTH [1–36]amide

This peptide is assembled in a stepwise manner on a polystyrene based resin support. The Fmoc-group is used for protection of the alpha-amino groups. Side-chain functional groups are protected as Glu(OtBu), Asp(OtBu), Ser(tBu), Lys(Boc), Arg(Pmc), and His(Trt). Other amino acids are left unprotected.

4-(2',4'-Dimethoxyphenyl-Fmoc-amino-methyl)-phenoxy-co(polystyrene-divinylbenzene), 0.4 mmol/g, which may be prepared, e.g., as described in Tetrah. Letters, 28, 3787–3790 (1987) is subjected to the following cycle, steps (1) to (5), of treatments:

(1) DMF
(2) piperidine (20%) in DMF
(3) DMF
(4) mixture of HOBt, diisopropylcarbodiimide, and Fmoc-alanine (0.8 mmol per gram starting resin each)
(5) DMF Volumes of washes and reagents are from 5 to 20 ml per gram of starting resin.

In the next cycle of treatments (1) to (5), Fmoc-valine is substituted for Fmoc-alanine and so on for each cycle such as to assemble on the resin the correct amino acid sequence of the title compound.

Each step is repeated as many times as necessary for either complete reaction of the resin (steps 2, 4) or complete displacement of the previous reagent(s) from the resin (steps 3, 5). Samples of the resin are removed after each cycle and checked for completeness of the coupling reaction by a colorimetric test for residual amino groups using a ninhydrin reagent. At the end of the synthesis, a terminal cycle consisting of steps (1) to (3) only is performed, the peptide resin washed with 2-propanol, then with a mixture of methanol and methylene chloride (1:1 v/v) and dried throughly in a vacuum desiccator. The peptide resin (1 g) is suspended in a mixture (20 ml) of trifluoromethane-sulfonic acid, TFA, p-cresole, dimethylsulfide, and 1,2-ethanedithiol (10:50:8:30:2 v/v) for 15 minutes at room temperature, the resin particles are filtered off and washed with some TFA containing 2% of 1,2-ethanedithiol. The product is precipitated from the combined filtrates by addition of ether (20 volumes), filtered, washed with more ether and dried. The product is chromatographied on a C-18 silica column using a gradient of acetonitrile in 2% H3PO4. Fractions are checked by analytical HPLC and those containing the pure compound are collected, filtered through an anion-exchange resin in the acetate form and lyophilised to give the title compound as a polyacetate, polyhydrate.

EXAMPLE 15: hPTH (1–36)

This peptide is similarly assembled in a stepwise manner on a polystyrene based resin support. Protecting groups are as in Example 14. 4-Hydroxymethyl-phenoxymethyl-co-(polystyrene-divinylbenzene), 0.6 mmol/g, which may be prepared, e.g. as described in J.Org.Chem 46, 3433–3436 (1981), is reacted with a mixture of Fmoc-alanine (1.8 mmol/g resin), 1-hydroxybenzotriazole (0.6 mmol/g resin), N,N'-dicyclohexylcarbodiimide (1.8 mmol/g resin) and 4-dimethylaminopyridine (0.6 mmol/g resin) in DMF (2 ml/g resin) and DCM (8 ml/g resin) for 16 hours. The resin is filtered off and washed with a mixture of DMF and DCM (1:4 v/v) then with DMF. It is subjected to the same cycle of treatments (1) to (5) as described in Example 1 starting with Fmoc-valine in step (4) of the first cycle and substituting the Fmoc-amino acid in each following cycle such as to assemble the correct amino acid sequence of the title compound.

The peptide is cleaved from the resin and purified as in Example 14 to give the title compound as a polyacetate, polyhydrate.

EXAMPLE 16: [Leu$^{36}$]h-PTH (1–36)amide

The title compound is prepared according to the procedure disclosed in Example 14 starting with Fmoc-leucine. $[\alpha]_D^{20}$=–17.1° (c=0.51 in 95% AcOH)

EXAMPLE 17

The procedure of any one of Examples 1 to 10 and 13 is repeated but using [1–36]hPTH instead of [1–38]hPTH.

We claim:

1. A compound of formula I

H—X$_1$—Val—Ser—Glu—Ile—Gln—Leu—Met—His—Asn—
Leu—Gly—Lys—His—Leu—Asn—Ser—Met—Glu—Arg—Val—
Glu—Trp—Leu—Arg—Lys—Lys—Leu—Gln—Asp—Val—His—
Asn—Phe—Val—X$_2$—X$_3$ wherein X$_1$ is Ser or Ala, X$_2$ is Leu or Ala, and X$_3$ is OH or NH$_2$ in free form or in the form of a salt or complex.

2. A pharmaceutical composition comprising a compound of formula I as defined in claim 1 in free form or in pharmaceutically acceptable salt form or complex form in association with a pharmaceutically acceptable carrier or diluent.

3. A method for preventing or treating osteoporosis, in a subject in need of such treatment, which method comprises administering to said subject an effective amount of a compound of formula I as defined in claim 1 or a pharmaceutically acceptable salt or complex thereof.

4. The compound of claim 1 wherein said salt form and complex form are pharmaceutically acceptable.

5. The composition of claim 2 wherein said composition is the form of a nasal spray, drop, gel, powder or insert.

6. The method of claim 3 wherein said compound or pharmaceutically acceptable salt or complex thereof is administered nasally.

7. A method for stimulating bone resorption and for stimulating bone cell proliferation, in a subject in need of such stimulation, comprising administering to said subject an effective amount of a compound of formula I as defined in claim 1 or a pharmaceutically acceptable salt or complex thereof.

8. The method of claim 7 wherein said compound or pharmaceutically acceptable salt or complex thereof is administered nasally.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( i x ) FEATURE:
        ( A ) NAME/KEY: Modified-site
        ( B ) LOCATION: 38
        ( D ) OTHER INFORMATION: /note="This terminal glycine ends
           either with a normal carboxy group or with an
           amide group."

( x i ) SEQUENCE DESCRIPTION: SEQ ID NO:1:

```
Ser  Val  Ser  Glu  Ile  Gln  Leu  Met  His  Asn  Leu  Gly  Lys  His  Leu  Asn
1                   5                        10                        15

Ser  Met  Glu  Arg  Val  Glu  Trp  Leu  Arg  Lys  Lys  Leu  Gln  Asp  Val  His
                    20                       25                        30

Asn  Phe  Val  Ala  Leu  Gly
               35
```

( 2 ) INFORMATION FOR SEQ ID NO:2:

( i ) SEQUENCE CHARACTERISTICS:
        ( A ) LENGTH: 36 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (ix) FEATURE:
(A) NAME/KEY: Region
(B) LOCATION: 1
(D) OTHER INFORMATION: /note="Amino acid 1 is either Ser or Ala."

(ix) FEATURE:
(A) NAME/KEY: Region
(B) LOCATION: 36
(D) OTHER INFORMATION: /note="Amino acid 36 is either Leu or Ala."

(ix) FEATURE:
(A) NAME/KEY: Modified-site
(B) LOCATION: 36
(D) OTHER INFORMATION: /note="Amino acid 36 ends either with a normal carboxy group or with an amide group."

(xi) SEQUENCE DESCRIPTION: SEQ ID NO:2:

Xaa Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Xaa
        35